United States Patent [19]

Lutz et al.

[11] 4,025,538

[45] May 24, 1977

[54] 2,6-DINITROANILINE HERBICIDES

[75] Inventors: Albert William Lutz, Montgomery Township, Somerset County; Robert Eugene Diehl, Trenton, both of N.J.

[73] Assignee: American Cyanamid Company, Stamford, Conn.

[22] Filed: July 25, 1975

[21] Appl. No.: 599,224

Related U.S. Application Data

[60] Division of Ser. No. 323,000, Jan. 12, 1973, Pat. No. 3,920,742, which is a continuation-in-part of Ser. No. 262,807, June 14, 1972, abandoned, which is a continuation-in-part of Ser. No. 174,938, Aug. 25, 1971, abandoned.

[52] U.S. Cl. .................................................. 260/397.6
[51] Int. Cl.² ........................................ C07C 147/00

[58] Field of Search ............................... 260/397.6

[56] References Cited

UNITED STATES PATENTS

| | | | |
|---|---|---|---|
| 2,158,648 | 5/1939 | Zerweck et al. | 260/576 |
| 2,469,695 | 5/1949 | McNally et al. | 260/490 |
| 3,546,295 | 12/1970 | Maravetz | 260/397.6 |
| 3,686,230 | 8/1972 | Maravetz | 260/397.6 |

*Primary Examiner*—Albert T. Meyers
*Assistant Examiner*—D. W. Robinson
*Attorney, Agent, or Firm*—H. G. Jackson

[57] ABSTRACT

This invention relates to certain substituted 2,6-dinitroaniline compounds. It further relates to certain pre-emergence herbicidal methods and compositions employing substituted 2,6-dinitroaniline compounds.

10 Claims, No Drawings

2,6-DINITROANILINE HERBICIDES

This application is a division of application Ser. No. 323,000, filed Jan. 12, 1973, (now U.S. Pat. No. 3,920,742) which was a continuation-in-part of application Ser. No. 262,807 filed June 14, 1972 (now abandoned), which in turn was a continuation-in-part of application Ser. No. 174,938 filed Aug. 25, 1971 (now abandoned).

This invention relates to certain substituted 2,6-dinitroaniline compounds. It further relates to certain pre-emergence herbicidal methods and compositions employing substituted 2,6-dinitroaniline compounds.

The novel 2,6-dinitroaniline compounds of the present invention may be represented by the following structural formula:

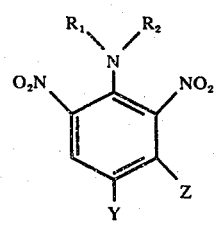

I wherein,

Y represents halogen, alkyl $C_1$–$C_4$, alkenyl $C_2$–$C_4$, $CF_3$, CN or —$SO_2NR_3R_4$;

Z represents alkyl $C_1$–$C_4$, alkenyl $C_2$–$C_4$ or mono-substituted alkyl $C_1$–$C_4$ where the substituent is halogen, alkoxy $C_1$–$C_4$ or —$NR_3R_4$;

$R_1$ represents hydrogen, alkyl $C_1$–$C_6$, alkenyl $C_2$–$C_6$ or alkynyl $C_2$–$C_6$;

R represents alkyl $C_2$–$C_7$ (straight, branched or cyclo), alkenyl $C_2$–$C_6$, alkynyl $C_2$–$C_6$, or mono-substituted alkyl $C_1$–$C_4$ where the substituent is halogen or alkoxy $C_1$–$C_4$;

$R_3$ and $R_4$ each represent hydrogen or alkyl $C_1$–$C_4$; and when $R_1$ and $R_2$ are taken together they represent piperidino, pyrrolidino or morpholino;

with the proviso that when Y and Z are methyl and $R_1$ is hydrogen or ethyl, then $R_2$ cannot be ethyl.

The above-identified compounds are highly effective herbicidal agents and particularly efficacious are those represented by the following structural formula:

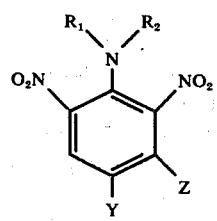

II wherein,

Y represents $CH_3$, $CF_3$, Cl, CN or $SO_2NHCH_3$;
Z represents $CH_3$;
$R_1$ represents alkyl $C_1$–$C_4$ or hydrogen;
$R_2$ represents alkyl $C_2$–$C_6$ (straight, branched or cyclo, but preferably branched), monohaloalkyl $C_3$–$C_4$, or alkoxyalkyl where the alkyl group is $C_3$–$C_4$ and the alkoxy is $C_1$–$C_4$; with the proviso that when Y and Z are methyl and $R_1$ is hydrogen or ethyl, then $R_2$ cannot be ethyl.

These compounds represent a preferred class of compounds within the above-broader generic class and show a marked superiority in herbicidal performance.

Illustrative lower alkyl substituents are methyl, ethyl, n-propyl, iso-propyl, n-butyl, t-butyl, n-pentyl, n-hexyl, 2-pentyl, 3-pentyl, sec-butyl, and the like.

Illustrative loweralkenyl substituents ae ethenyl, 1-propenyl, 2-propenyl, 1-butenyl, 2-butenyl, 3-butenyl, 1-pentenyl, 1-hexenyl, and the like.

Illustrative loweralkynyl substituents are ethynyl, 1-propynyl, 2-propynyl, 1-butynyl, 2-butynyl, 3-butynyl, 1-pentynyl, 1-hexynyl, and the like.

Illustrative cyclic hydrocarbons are cyclopropyl, cyclobutyl, cyclopentyl, and cyclohexyl groups.

Illustrative halogen substituents are fluoro, chloro, bromo and iodo groups.

The herbicidal methods of the present invention comprise application of a herbicidally effective amount of one or more compounds of Formula III below to the soil containing the seeds of undesirable plant species to be controlled.

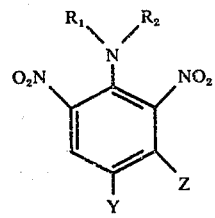

III wherein,

Y represents halogen, alkyl $C_1$–$C_4$, alkenyl $C_2$–$C_4$, $CF_3$, CN, or —$SO_2NR_3R_4$;

Z represents alkyl $C_1$–$C_4$, alkenyl $C_2$–$C_4$ or mono-substituted alkyl $C_1$–$C_4$ where the substituent is halogen, alkoxy $C_1$–$C_4$ or —$NR_3R_4$;

$R_1$ represents hydrogen, alkyl $C_1$–$C_6$, alkenyl $C_2$–$C_6$ or alkynyl $C_2$–$C_6$;

$R_2$ represents alkyl $C_1$–$C_7$ (straight, branched or cyclo), alkenyl $C_2$–$C_6$, alkynyl $C_2$–$C_6$, or mono-substituted alkyl $C_1$–$C_4$ where the substituent is halogen or alkoxy $C_1$–$C_4$;

$R_3$ and $R_4$ each represent hydrogen or alkyl $C_1$–$C_4$; and when $R_1$ and $R_2$ are taken together they represent piperidino, pyrrolidino or morpholino.

Wherein an asymmetric carbon atom exists in the dinitroaniline compounds above, optical isomerism may exist. Accordingly, such compounds may be employed as separate antimers or in admixture, as in a racemic composition. Unless there is indication to the contrary by reference to such a compound, the unresolved composition is intended herein. Separation of antimers, where desired, may be effected by convention resolution techniques. A convenient method relates to the introduction of an optically active substituent, such as a (—)-sec-butylamino group into the ring system, as by nucleophilic substitution, as exemplified below.

Preferably, application of these compounds, or active ingredients is made using the herbicidal compositions described below with conventional application methods.

The 2,6-dinitroaniline compounds are prepared by a nucleophilic substitution of a 1-substituent, such as, a chloro group, with the appropriately substituted amine. While chloro is a preferred substituent, and the discussion is in terms thereof other conventional equivalent substituents, such as, bromo or iodo are included herein. The displacement may be conducted with or without an organic solvent, such as toluene, benzene or preferably xylene.

The reaction, which is graphically illustrated below, is carried out by heating the reactants, preferably between 50° C. and 150° C.

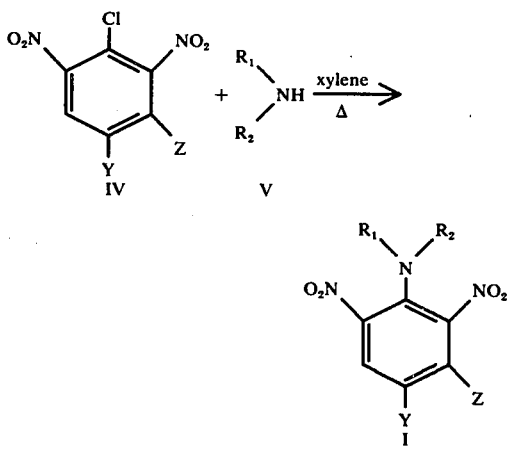

For purposes of further discussion, the active ingredients may be considered as falling into one of six classes of compounds, labeled as Types A through F. In Type A compounds, Y is alkyl $C_1$–$C_4$. In Type B compound, Y is alkenyl $C_2$–$C_4$. In Type C compounds, Y is halogen and preferably chlorine or bromine. In Type D compounds, Y is —$SO_2NR_3R_4$, where $R_3$ and $R_4$ are as described above. In Type E compounds, Y is trifluoromethyl. In Type F compounds, Y is CN.

Type A compounds, where Y and Z are loweralkyl groups, can be prepared by reacting the appropriately substituted 2,6-dinitrochlorobenzene with the appropriate amine.

The chlorobenzene intermediates for Type A compounds can be prepared by reacting an appropriately substituted aniline with ethyl chloroformate in benzene at about 10° C. to 50° C. to yield the correspondingly substituted N-(ethoxycarbonyl)-3,4-substituted aniline. This product is then treated with a cold solution of sulfuric and nitric acid, i.e., at about 0° C. to 20° C. to obtain the N-(ethoxycarbonyl)-3,4-disubstituted-2,6-dinitroaniline. Reaction of the thus-formed product with sulfuric acid at an elevated temperature, preferably between about 100° C. and 150° C., converts the N-(ethoxycarbonyl) product to the 3,4-disubstituted-2,6-dinitroaniline. The amino group is replaced by a chlorine atom by first heating the compound with glacial acetic acid and diazotizing the amine with a mixture of sodium nitrite in sulfuric acid. This is followed by treating the diazotized mixture with a mixture of cuprous chloride in hydrochloric acid, and then heating the thus-formed mixture to about 40° C. to 80° C. to obtain the chlorinated compound.

Selected chlorinated intermediates for Type A compounds can also be prepared by reacting a mixture of fuming sulfuric acid and fuming nitric acid with 4-chloro-o-xylene at about 10° C. to 60° C., pouring the mixture over ice and separating the precipitated solid. Recrystallization of the solid from methanol or other loweralkyl alcohol $C_1$–$C_4$ yields the high purity product.

Illustrative Type A compounds which are readily prepared by the preceding procedure include, for example: 3,4-dimethyl-2,6-dinitro-N,N-di-n-propylaniline; N-ethyl-N-n-propyl-3,4-dimethyl-2,6-dinitroaniline; N,N-di-n-butyl-3,4-dimethyl-2,6-dinitroaniline; 3,4-dimethyl-2,6-dinitro-N-oxydiethyleneaniline; 3,4-dimethyl-2,6-dinitro-N-pentamethyleneaniline; 3,4-dimethyl-2,6-dinitro-N-tetramethyleneaniline; N,N-dicyclopropyl-3,4-dimethyl-2,6-dinitroaniline; N,N-diallyl-3,4-dimethyl-2,6-dinitroaniline; N-ethyl-N,3,4-trimethyl-2,6-dinitroaniline; N,3,4-trimethyl-2,6-dinitro-N-(cyclopropyl)aniline; N,N-dipropargyl-3,4-dimethyl-2,6-dinitroaniline; N,N-bis(1-buten-3-yl)-3,4-dimethyl-2,6-dinitroaniline; N-ethyl-3-isopropyl-4-methyl-2,6-dinitroaniline; 3-sec-butyl-4-methyl-2,6-dinitro-N,N-dimethylaniline, N,N,3,4-tetramethyl-2,6-dinitroaniline; N,N-diethyl-3,4-dimethyl-2,6-dinitroaniline; N,3,4-trimethyl-2,6-dinitro-N-propylaniline; N-cyclobutyl-N,3,4-trimethyl-2,6-dinitroaniline; 3,4-dimethyl-2,6-dinitro-N,N-(dicyclopropylmethyl)aniline; N,3,4-trimethyl-2,6-dinitroaniline; N-ethyl-3,4-dimethyl-2,6-dinitroaniline; 3,4-dimethyl-2,6-dinitro-N-(cyclopropyl)aniline; N-isopropyl-3,4-dimethyl-2,6-dinitroanilinee; N-allyl-3,4-dimethyl-2,6-dinitroaniline; N-n-butyl-3,4-dimethyl-2,6-dinitroaniline; N-sec-butyl-3,4-dimethyl-2,6-dinitroaniline; and 3,4-dimethyl-2,6-dinitro-N-3-pentylaniline.

The 3,4-diethyl derivatives, 3-methyl-4-ethyl derivatives, 3-ethyl-4-methyl, 3-ethyl-4-propyl, 3,4-diisopropyl, 3,4-di-n-propyl, 3,4-di-n-butyl, 3,4-diisobutyl, 3-propyl-4-butyl, and 3-methyl-4-isopropyl derivatives of the above-named 2,6-dinitroanilines, are likewise prepared by the above procedure, utilizing the appropriate 3,4-disubstituted-2,6-dinitrochlorobenzene and appropriate amine.

Type B compounds, where Y represents a lower alkenyl $C_2$–$C_4$ group, are prepared by the procedure described above. The reaction is preferably run in xylene at a temperature between about 50° C. and 150° C. and involves the reaction of a 3-substituted-4-alkenyl-2,6-dinitrochlorobenzene with the appropriate amine. In this reaction, Z is preferably methyl or ethyl, although it may be any of the radicals previously described for it.

Illustrative Type B compounds, which can be prepared by this procedure include, for example: N-sec-butyl-4-isobutenyl-3-methyl-2,6-dinitroaniline; 4-isopropenyl-3-methyl-2,6-dinitro-N,N-di-n-propylaniline; N,3-di-methyl-2,6-dinitro-4-n- propenylaniline; and 4-isopropenyl-N,N,3,5-tetramethyl-2,6-dinitroaniline.

A preferred method for the preparation of Type C compounds wherein Y is halogen and Z is lower alkyl involves the reaction of a dihalo-dinitroalkylbenzene, such as 3,6-dihalo-2,4-dinitrotoluene, with the appropriate amine. The reaction is preferably carried out in the presence of an organic solvent, such as $C_1$–$C_4$ alcohols, toluene and the like. The reaction may be conducted at room temperature, although heating is generally advantageously employed.

Type C compounds having the following structure may be prepared by the process described in *Chemical Abstracts* 44: 1433g; 66: 109, 220k; amd 54: 9921c:

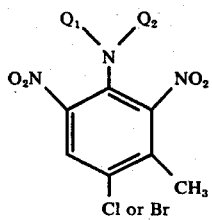

VI where $Q_1$ and $Q_2$ are hydrogen or methyl.

Type D compounds, in which Y represents an —$SO_2NR_3R_4$ group, can be synthesized by reacting, at an elevated temperature, a 1-chloro-3-substituted-2,6-dinitro-4-sulfonamide or alkyl-substituted sulfonamide with an amide, preferably in an organic solvent, such as xylene, toluene or the like. The intermediates for this reaction can be prepared by reacting m-chlorotoluene with sulfuric acid and potassium nitrate to form the potassium 4-chloro-3,5-dinitro-o-toluenesulfonate which is converted to the corresponding o-toluenesulfonyl chloride by reaction with phosphorus pentachloride and phosphorus oxychloride. The thus-formed toluenesulfonyl chloride is then treated with ammonia, alkylamine or dialkylamine in acetone at 0° C. to 25° C. to obtain the corresponding o-toluenesulfonamide. Treatment of this product with the appropriate amine (i.e.,

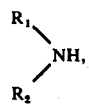

where $R_1$ and $R_2$ are as described above) then yields the 4-sulfamoyl or alkyl-substituted sulfamoyl-2,6-dinitroaniline of this invention.

Illustrative Type D compounds which can be prepared by the process of the instant invention are: 3-methyl-2,6-dinitro-$N^4$,$N^4$-di-n-propyl-4-sulfamoylaniline; $N^4$-sec-butyl-3-methyl-4-(methylsulfamoyl)-2,6-dinitroaniline; 4-(dimethylsulfamoyl)-3-methyl-2,6-dinitro-$N^4$-3-pentylaniline; $N^4$,3-dimethyl-2,6-dinitro-4-sulfamoylaniline; 3-methyl-$N^4$-oxydiethylene-2,6-dinitro-4-sulfamoylaniline; 3-methyl-4-(methylsulfamoyl)-2,6-dinitro-$N^4$-pentamethyleneaniline, 3,5-dimethyl-4-(methylsulfamoyl)-2,6-dinitro-$N^4$-tetramethyleneaniline.

Type E compounds can be prepared by reacting the appropriate 3-substituted-4-trifluoromethyl-2,6-dinitrochlorobenzene with the appropriate amine, preferably by heating the reactants in the presence of an organic solvent such as benzene, toluene or the like.

Preparation of chlorobenzene intermediates for use in this reaction are described by Newman and Pinkus, *Journal of Organic Chemistry* 19: 978, and Von Auwers and Julicker, *Chemische Berichte* 55: 2167 (1922). For example, 4-methylphenol may be treated with aluminum trichloride in carbon tetrachloride to obtain 2,5-cyclohexadien-1-one which is treated with phosphoruspentachloride to yield 3-methyl-4-trichloromethylchlorobenzene. When the latter compound is treated with $SbF_3$, 1-chloro-3-methyl-4-(trifluoromethyl)benzene is obtained. This product may be nitrated using a mixture of nitric acid and sulfuric acid to give the intermediate, 1-chloro-3-methyl-2,6-dinitro-4-(trifluoromethyl)benzene.

Illustrative Type E compounds which can be prepared by this process include, for example: 3-methyl-2,6-dinitro-N,N-di-n-propyl-4-(trifluoromethyl)aniline; N-sec-butyl-3-methyl-2,6-dinitro-4-(trifluoromethyl)aniline; 3-methyl-2,6-dinitro-N-3-pentyl-4-(trifluoromethyl)aniline; N-cyclopropyl-3-methyl-2,6-dinitro-4-(trifluoromethyl)aniline; and 3-ethyl-2,6-dinitro-N-isopropyl-4-(trifluoromethyl)aniline.

Type F compounds are prepared by reacting the appropriate 3,5-disubstituted-4-cyano-2,6-dinitrochlorobenzene with the appropriate amine.

o-Toluoyl chlorides may be prepared by reacting 3,5-dinitro-4-chloro-o-toluic acid with phosphorus pentachloride. The resulting o-toluoyl chloride is then treated with ammonia in cold acetone to yield the corresponding 3,5-dinitro-4-chloro-o-toluamide which is converted to the corresponding nitrile by reaction with phosphorus pentoxide or preferably with $POCl_3$.

The preemergence herbicidal compositions of the present invention are solid or liquid formulations comprising an effective amount of one or more of the 2,6-dinitroaniline compounds of Formula I, or preferably Formula II, and those compounds corresponding to Formula I wherein $R_2$ also represents methyl with a herbicidal adjuvant, i.e., an inert carrier or other conventional formulation aid.

Preparation of said compositions broadly involves admixing an effective amount of the herbicidal agent and adjuvant.

Use of said compositions broadly involves application of an effective amount of said compounds or preferably said compositions to the soil containing seeds of the plants to be controlled.

Typical formulations include, for example, dusts, dust concentrates, wettable powders, granulars, and the like. Application by conventional methods and equipment is usually made at rates of from about ⅛ pound per acre to about 20 pounds per acre and preferably ¼ to 8 pounds per acre of active material.

Dusts are generally prepared by grinding together from about 1% to 15% by weight of the active material with from about 99% to 85% by weight of a solid diluent, such as an attaclay, kaolin, diatomaceous earth, fullers earth, talc, pumice or the like.

Dust concentrates are prepared in similar fashion to the dusts excepting that generally about 15% to about 95% by weight of active material is used.

Granular formulations may be prepared by applying a liquid solution of the active material to sorptive granular carriers, such as attaclay, kaolin, or diatomite granules. Alternatively, they may be mixed with inert carriers and applied to non-sorptive granules, such as sand or limestone.

Wettable powders are prepared by grinding the active ingredient with a solid carrier, such as used in the dust formulations. Usually, about 25% to 75% by weight of the active material and from about 73% to 23% by weight of solid carrier is used. In addition, there is generally added about 1% to 5% by weight of a dispersing agent, such as alkali metal salts of naphthalene sulfuric acid and anionic-nonionic blends, and from about 1% to 5% by weight of a surfactant, such as polyoxyethylene alcohols, acids, adducts, sorbitan fatty acid esters and sorbitol esters. Typical formulations by weight percent are given below.

TABLE I

| | Typical Wettable Powder Formulations |
|---|---|
| A | Ingredientstz,1/32 |
| 25% | 3,4-dimethyl-2,6-dinitro-N-3-pentylaniline |
| 65% | attaclay |
| 5% | sodium lignosulfonate |
| 5% | sodium N-methyl-N-oleoyl taurate |
| B | Ingredients |
| 33% | N-sec-butyl-3,4-dimethyl-2,6-dinitroaniline |
| 59% | attaclay |
| 5% | sodium lignosulfonate |
| 3% | alkyl phenoxy polyoxyethylene ethanol |
| C | Ingredients |
| 40% | 3,4-dimethyl-2,6-dinitro-N,N-dipropylaniline |
| 50% | precipitated hydrated silicon dioxide (Hi Sil)[a] |
| 5% | sodium lignosulfonate |
| 3% | anionic-nonionic blend (MAL-77L)[b] |
| 2% | wetting agent |

[a]By Pittsburgh Plate Glass Company
[b]By Wm. Cooper and Nephews

The wettable powder formulations are usually dispersed in water and applied as a liquid spray to the area or locus where control of undesirable plant species is desired.

For use as preemergence herbicides, the dusts or liquid sprays containing the active compound can be applied to the soil shortly after planting or they may be incorporated into the soil by the technique referred to as preplant incorporation.

The practice and advantages of the present invention and preparation of the active ingredients used therein is further illustrated by the following examples which are not to be taken as being limitative thereof. Parts and percentages herein are by weight unless otherwise indicated.

EXAMPLE 1

Preparation of 3,4-Dimethyl-2,6-dinitrochlorobenzene

Two grams of 3,4-dimethyl-2,6-dinitroaniline [Chemical Abstracts 44: 4447 (1950)] is dissolved in 40 ml. of warm glacial acetic acid. The solution is cooled to room temperature and a mixture of 0.9 grams of sodium nitrite in 7 ml. of concentrated sulfuric acid is added very slowly leaving a solid in the mixture. This mixture is then added to a solution of cuprous chloride in concentrated hydrochloric acid. The cuprous chloride solution is prepared by dissolving 3.24 grams of $CuSO_4 \cdot 5H_2O$ in water and adding NaCl to the warm solution. While holding the blue solution in an ice bath, a solution of 1.24 grams of sodium meta-bisulfite and 0.52 grams of NaOH in 12 ml. of water is added. A white precipitate forms and is dissolved in 12 ml. of concentrated hydrochloric acid. The diazonium mixture is then warmed, filtered, and the solid collected and recrystallized from cyclohexane. The product has a melting point of 109° C. to 111° C. The procedures are repeated using 16 grams of the amine, yielding 11 grams of product, having a melting point of 111° C. to 113° C.

EXAMPLE 2

Preparation of 3,4-Dimethyl-2,6-dinitrochlorobenzene

Fuming sulfuric acid (750 ml., 23%) and fuming nitric acid (240 ml., 90%) are mixed at 0° C. to 45° C. Then 4-chloro-o-xylene (270 grams, 1.93 moles) is added at 10° C. to 60° C. When the addition is complete, the reaction mixture is poured into 8000 ml. of ice and 4000 ml. water and then filtered. The cake is washed with 4000 ml. of water, 500 ml. methanol, and finally 500 ml. of petroleum ether. The cake is then slurried two times with 200 ml. xylene and filtered. The filter cake is then washed with 50 ml. cold xylene and 300 ml. of methanol at 50° C. The solid is then recrystallized from 2500 ml. of methanol and washed with 2 pints of petroleum ether. The yield of white solid is 120 grams with melting point 112° C. to 113° C.

EXAMPLE 3

Preparation of 3,4-Dimethyl-2,6-dinitro-N,N-di-n-propylaniline

Five grams of 1-chloro-3,4-dimethyl-2,6-dinitrobenzene and 5.05 grams of di-n-propylamine are dissolved in benzene and the mixture is refluxed. The benzene is then removed from the mixture by boiling and toluene is added to the remaining residue. The thus-formed mixture is then refluxed, filtered, and the filtrate stripped in vacuo. The residue is treated with hexane and the mixture chilled in dry ice and acetone. The solid from the mixture is collected and dried, it has a melting point of 42° C. to 43.5° C. and is the desired product.

EXAMPLE 4

Preparation of N-Isopropyl-3,4-dimethyl-2,6-dinitroaniline

4-Chloro-3,5-dinitro-o-xylene (10.0 grams, 0.043 mole) and i-propylamine (10.1 grams, 0.17 mole) are mixed and refluxed for 12 hours using an efficient reflux condenser. The mixture is then cooled and poured into 100 ml. of 5% hydrochloric acid and extracted with diethyl ether. The ether extract is dried over magnesium sulfate. Removal of the drying agent and solvent leaves an orange oil which readily solidifies. The product is recrystallized from methanol to give 8.7 grams (80%) of an orange solid with melting point 69° C. to 70° C.

EXAMPLE 5

Preparation of N-sec-Butyl-3,4-diethyl-2,6-dinitroaniline

A mixture of 4-chloro-3,5-dinitro-o-xylene (140 grams, 0.61 mole), mono-sec-butylamine (184 ml., 1.82 moles), and xylene (1400 ml.) is brought to reflux. After refluxing overnight, the reaction mixture is cooled and filtered. The precipitate is washed with petroleum ether. The filtrate and washings are combined, washed with 500 ml. of 10% hydrochloric acid, and finally with 2 liters of water. The organic layer is separated and dried. Removal of the drying agent and the solvent leaves an orange oil which crystallizes with the addition of petroleum ether. A yellow orange solid (150.6 grams, 86.5%) with melting point 42° C. to 43° C. is collected.

EXAMPLES 6 to 50

Following the general procedures of Examples 4 and 5, substituting the appropriate amine for the amines used therein, yields products having the following formula and properties set forth in Table II below.

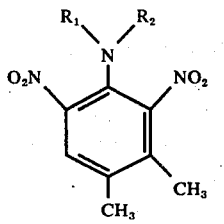

VII

TABLE II

| Example Number | Substituents R₁ | R₂ | Melting Point °C. | Crystallizing Solvent |
|---|---|---|---|---|
| 6 | H | H | 141–142 | ethanol |
| 7 | H | $C_3H_7$-n | 71–71.5 | cyclohexane |
| 8 | $C_4H_9$ | $C_2H_5$ | oil | |
| 9 | $CH_2CH=CH_2$ | $CH_2CH=CH_2$ | 41–42 | hexane/petroleum ether |
| 10 | $CH_3$ | $CH_3$ | 84–85 | methanol |
| 11 | morpholino | | 118–119 | methanol |
| 12 | $C_3H_7$ | $C_3H_7$ | 42–43.5 | hexane |
| 13 | H | $CH_2C(CH_3)_3$ | 88–89 | methanol |
| 14 | H | $CHCH_2CH_2CH(CH_3)_2$ \| $CH_3$ | 79–80 | |
| 15 | H | $CH(CH_2CH_2CH_3)_2$ | 48–49 | |
| 16 | H | $CHC_4H_9$-t \| $CH_3$ | 100–101 | |
| 17 | $C_2H_5$ | $C_2H_5$ | oil | |
| 18 | H | $CH-C_3H_7$-n \| $C_2H_5$ | 40–42 | |
| 19 | H | $C_6H_{13}$-n | oil | |
| 20 | H | $C_4H_9$-n | 68–71 | methanol |
| 21 | H | $CHC_2H_5$ \| $CH_3$ | 43–44 | hexane |
| 22 | $C_4H_9$-n | $C_4H_9$-n | 30–31 | methanol |
| 23 | H | $CH(CH_3)_2$ | 67–68 | $H_2O$/methanol |
| 24 | H | $CH_2CH(CH_3)_2$ | 46–47 | methanol |
| 25 | H | $CH_2CH=CH_2$ | 81–82 | methanol |
| 26 | H | $CHCH_2CH(CH_3)_2$ \| $CH_3$ | 81–82 | methanol |
| 27 | $C_2H_5$ | $CH_2CH_2CH_3$ | oil | |
| 28 | H | $CH(C_2H_5)_2$ | 56–57 | methanol |
| 29 | H | $CHCH_2CH_2CH_3$ \| $CH_3$ | 42–43 | methanol |
| 30 | H | $CH_2CH_2CH(CH_3)_2$ | 48–50 | methanol |
| 31 | cyclohexyl | | 106–108 | cyclohexane |
| 32 | cyclopentyl | | 120–122 | cyclohexane |
| 33 | H | $CH-CH(CH_3)_2$ \| $CH_3$ | 61–63 | methanol |
| 34 | H | $C(CH_3)_3$ | 66–67 | hexane |
| 35 | H | $CH_2CH-C_2H_5$ \| $CH_3$ | 44–45 | |
| 36 | H | $CH-C\equiv CH$ \| $CH_3$ | | |
| 37 | H | $CH_2C(CH_3)_3$ | 88–89 | methanol |
| 38 | H | $CH(CH_3)C(CH_3)_3$ | 100–101 | methanol |
| 39 | H | $CH(CH_2)_2CH(CH_3)_2$ \| $CH_3$ | 79–80 | methanol |
| 40 | H | $CH(C_3H_7$-n$)_2$ | 48–49 | methanol |
| 41 | $CH_3$ | cyclohexyl | 57–60 | petroleum ether |
| 42 | H | $CHC_4H_9$-n \| $CH_3$ | 51–53 | |
| 43 | H | $CHCH_2OCH_3$ \| $CH_3$ | oil | |
| 44 | $CH_3$ | $CH_2CH_2Cl$ | oil | |
| 45 | H | $CH_2CH(OCH_3)_2$ | 72–73 | |
| 46 | H | $CH(C_2H_5)CH_2OCH_3$ | 46-47.5 | |
| 47 | H | $CH(CH_3)CH_2Cl$ | oil | |
| 48 | H | $CH(C_2H_5)CH_2Cl$ | oil | |
| 49 | H | $CH(C_2H_5)CH_2OC_2H_5$ | 47–49 | |
| 50 | H | $CH_2CH_2CH_2OCH_3$ | 43–44 | |

EXAMPLE 51

Preparation of N-(3-Hexyl)-4-allyl-3-methyl-2,6-dinitroaniline

One equivalent of 4-allyl-3-methyl-2,6-dinitrochlorobenzene is dissolved in three volumes of xylene containing two equivalents of 3-hexylamine. The mixture is refluxed for 5 hours and then poured into water. The organic phase is washed with 5% hydrochloric acid and then water, dried over calcium sulfate, and removed in vacuo to leave the above-named product.

EXAMPLE 52

Preparation of
4-Chloro-N-isopropyl-3-methyl-2,6-dinitroaniline

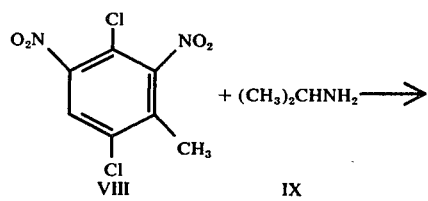

To a stirred mixture of 10.0 grams (0.04 mole) of 3,6-dichloro-2,4-dinitrotoluene in 50 ml. of ethanol is added 9.0 grams (0.15 mole) of isopropylamine. The mixture is stirred at room temperature for 2 hours and then at reflux for one hour. The solution is allowed to cool to room temperature and the crystalline precipitate is filtered and washed with a little hexane to give 10.2 grams of golden crystals, melting point 69° C. to 73° C. Two recrystallizations from methanol give the analytically pure compound, melting point 69° C. to 70° C.

EXAMPLE 53

Preparation of
4-Chloro-3-methyl-2,6-dinitro-N,N-dipropylaniline

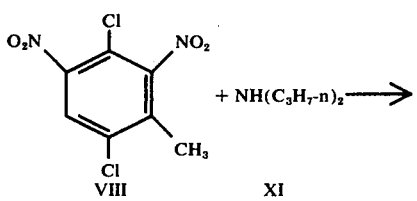

A solution of 10.04 grams (0.04 mole) of 3,6-dichloro-2,4-dinitrotoluene, 12.2 grams (0.12 mole) of di-n-propylamine, and 60 ml. of toluene is stirred at reflux for 9 hours. The mixture is cooled, diluted with ether, and extracted twice with dilute hydrochloric acid. The organic phase is then extracted consecutively with water, aqueous sodium bicarbonate, and brine and dried over magnesium sulfate. Evaporation of the solvent at reduced pressure gives 12.5 grams of an oil. Crystallization of the product from hexane gives 9.08 grams of yellow solid, melting point 36° C. to 38° C. The analytically pure compound, melting point 41° C. to 42° C., is obtained by recrystallization from 95% ethanol.

EXAMPLES 54 to 74

Following the general procedure of Example 45, substituting the appropriate amine for the di-n-propylamine used therein, yields compounds of the following structural formula having properties set forth in Table III below:

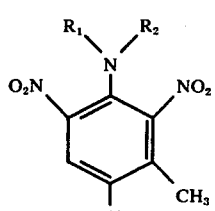

TABLE III

| Example Number | Substituents $R_1$ | $R_2$ | Melting Point °C. |
|---|---|---|---|
| 54 | H | H | 123–125 |
| 55 | H | $CH_2CH_2CH_3$ | 83.5–85 |
| 56 | H | $CH_2CH=CH_2$ | 61–62.5 |
| 57 | H | $CH(CH_3)_2$ | 69–70 |
| 58 | H | $CH_2CH(CH_3)_2$ | 52–55 |
| 59 | H | $CH_3$<br>$\|$<br>$CHCH_2CH_3$ | oil |
| 60 | H | $C(CH_3)_3$ | 41–46 |
| 61 | H | $CH(CH_2CH_3)_2$ | 41.5–44 |
| 62 | H | $CH_3$<br>$\|$<br>$CHCH_2CH_2CH_3$ | 31–32 |
| 63 | H | $(CH_2)_5CH_3$ | 32.5–34 |
| 64 | H | $CH_3$<br>$\|$<br>$CHCH_2CH(CH_3)_2$ | 62.5–65.5 |
| 65 | H | $CH_2CH_2CH_2OCH_3$ | 42.5–46.5 |
| 66 | H | $CH_2CH_2CN$ | 101–104 |
| 67 |  | cyclohexyl | 84–87 |
| 68 | H | phenyl | 93–94 |
| 69 | $CH_3$ | $CH_3$ | 67.5–70 |
| 70 | $C_2H_5$ | $C_2H_5$ | oil |
| 71 | $CH_2CH=CH_2$ | $CH_2CH=CH_2$ | oil |
| 72 | $CH_2CH_2CH_3$ | $CH_2CH_2CH_3$ | 41–43 |
| 73 |  | morpholino | 117–120.5 |
| 74 | H | $CH_2CH_2CH_2OCH_3$ | 43–47 |

EXAMPLE 75

Preparation of Potassium
4-Chloro-3,5-dinitro-o-toluenesulfonate m-Chlorotoluene (166 grams, 1.31 moles) is added to a mixture of 1000 ml. of concentrated sulfuric acid and 170 ml. of 23% fuming sulfuric acid and heated to 100° C. The solution is then cooled to 25° C. and potassium nitrate (400 grams) carefully added at 35° C. to 45° C. After the addition is complete, the reaction is stirred for one hour at 40° C. to 45° C. and then slowly heated to 100° C. and held between 100° C. and 110° C. for 1.5 hours. Finally, the reaction mixture is cooled and poured into 12,000 ml. of ice and the precipitated solid collected. The product is washed with water and then recrystallized from 5 liters of water. The crude yield of potassium salt is 305 grams.

EXAMPLE 76

Preparation of 4-Chloro-3,5-dinitro-o-toluenesulfonyl Chloride

Sixty grams of potassium 4-chloro-3,5-dinitro-o-toluenesulfonate, 70 grams of phosphorus pentachloride and 120 ml. of phosphorus oxychloride are mixed and refluxed for 3 hours. The mixture is filtered to remove some insoluble solid. The filtrate is carefully poured into water at 20° C. to 30° C. The precipitated solid is collected and dissolved in 500 ml. of benzene. The benzene solution is washed with water and then dried over $MgSO_4$. After removing the magnesium sulfate, the benzene is concentrated to 100 ml. and 400 ml. of hexane added. The precipitated solid is collected and recrystallized from 300 ml. hexane and 100 ml. of benzene to yield 50 grams of solid with melting point 105° C. to 107° C.

EXAMPLE 77

Preparation of 4-Chloro-3,5-dinitro-o-toluenesulfonamide

4-Chloro-3,5-dinitro-o-toluenesulfonyl chloride (10 grams, 0.0318 mole) is dissolved in 150 ml. of acetone and chilled to −15° C. Ammonia (1.08 grams, 0.064 mole) is condensed and then vaporized into the acetone solution. When the addition is complete, the reaction mixture is poured into an equal volume of water and the precipitated solid collected. The crude yield of white solid is 6.8 grams with melting point 205° C. to 215° C.

EXAMPLE 78

Preparation of 3-Methyl-2,6-dinitro-$N^1$,$N^1$-dipropylsulfanilamide

A mixture of 3.4 grams of 4-chloro-3,5-dinitro-o-toluenesulfonamide, N,N-dipropylamine (3.4 grams) and 50 ml. of toluene ae brought to reflux. At this point, everything is in solution. After refluxing 24 hours, the mixture is cooled, washed with water, dilute acid and finally water. The organic layer is then separated and dried over $MgSO_4$. Removal of the drying agent and solvent yields the desired product.

EXAMPLES 79 to 87

Following the general procedure of Example 78, substituting the appropriate amine and dinitrosulfonamide for N,N-dipropylamine and 4-chloro-3,5-dinitro-o-toluenesulfonamide, respectively, yields the products having the following structure and properties set forth in Table IV below:

TABLE IV

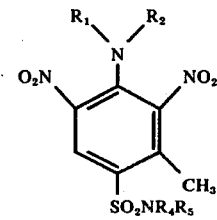

XIV

| Example Number | $R_1$ | $R_2$ | $R_4$ | $R_5$ | Melting Point ° C. |
|---|---|---|---|---|---|
| 79 | H | $C_4H_9$-sec | H | H | 126–129.5 |
| 80 | H | $C_3H_7$-n | H | H | 108–109 |
| 81 | H | H | H | H | 226–228 |
| 82 | $C_3H_7$-n | $C_3H_7$-n | H | $CH_3$ | 140–142 |
| 83 | $C_3H_7$-n | $C_3H_7$-n | $CH_3$ | $CH_3$ | 124–127 |
| 84 | $C_3H_7$-n | $C_3H_7$-n | H | —CH(CH$_3$)—$C_2H_5$ | 132–134 |
| 85 | $CH_3$ | H | H | $CH_3$ | 206–208 |
| 86 | H | $C_4H_7$-sec | H | $CH_3$ | 118–119 |
| 87 | H | $C_4H_7$-sec | H | $C_4H_9$-sec | 112–114 |

EXAMPLE 88

Preparation of N-sec-Butyl-3-methyl-2,6-dinitro-4-(trifluoromethyl)aniline

A nitration mixture, consisting of 16.1 ml. of $H_2SO_4$ (d 1.84) and 1.9 ml. of $HNO_3$ (d 1.5), is heated to 55° C. and 3.5 grams of 5-chloro-2-(trifluoromethyl)toluene is slowly added. The mixture is heated for one hour at 55° C. followed by one hour at 110° C. The reaction mixture is cooled and poured onto ice to give 5-chloro-2-(trifluoromethyl)-4,5-dinitrotoluene as a cream-colored solid. The product is crystallized from cyclohexane to give 3.6 grams of cream-colored crystals, melting point 81° C. to 82° C. 1.8 Grams of 5-chloro-2-(trifluoromethyl)-4,6-dinitrotoluene is refluxed for 15 minutes with 3 ml. of mono-sec-butylamine and 30 ml. of benzene, cooled, filtered, washed with water until neutral, dried and vacuum stripped to give 1.5 grams of N-sec-butyl-3-methyl-2,6-dinitro-4-(trifluoromethyl)aniline as a yellow solid, melting point 38° C. to 39° C.

EXAMPLES 89 to 93

Following the general procedure of Example 88, substituting the amine for the mono-sec-butylamine used therein, yields compounds having the following structural formula and the properties set forth in Table V below:

TABLE V

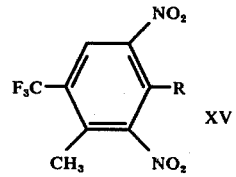

XV

| Example Number | Substituent R | Melting Point ° C. |
|---|---|---|
| 89 | —N($C_3H_7$)$_2$ | 32–35 |
| 90 | —NHCH($CH_3$)$_2$ | Yellow crystals 75–76 |

TABLE V-continued

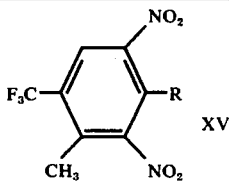

XV

| Example Number | Substituent R | Melting Point ° C. |
|---|---|---|
| 91 | —N(CH$_3$)$_2$ | Yellow crystals 107–108 |
| 92 | —N(C$_2$H$_5$)$_2$ | Orange brown oil |
| 93 | —NHCH(C$_2$H$_5$)$_2$ | 44–45 |

EXAMPLE 94

Preparation of 3,5-Dinitro-4-chloro-o-toluoyl Chloride

Ten grams of 3,5-dinitro-4-chloro-o-toluic acid is warmed on a water bath with 9.2 grams of phosphorus pentachloride and 30 ml. of benzene. After the solids dissolve, the benzene is distilled and the phosphorus oxychloride is removed under reduced pressure. The desired product as a residual oil solidifies on chilling.

EXAMPLE 95

Preparation of 3.5-Dinitro-4-chloro-o-toluamide 3,5-Dinitro-4-chloro-o-toluoyl chloride is treated with two equivalents of ammonia in cold acetone. The mixture is poured into water and the desired product as a precipitated solid collected by filtration.

EXAMPLE 96

Preparation of 3,5-Dinitro-4-chloro-o-toluonitrile

A finely powdered mixture of 15.5 grams (0.051 mole) of 3,5-dinitro-4-chloro-o-toluamide is heated with 12 grams (0.084 mole) of phosphorus pentoxide for 15 minutes at 300° C. to 350° C. The resulting nitrile is distilled from the reaction flask. Recrystallization of the solidified product from methanol gives the desired product as an analytically pure material.

EXAMPLES 97 to 98

Preparation of 4-Cyano-3-methyl-2,6-dinitro-N,N-dipropylaniline

A mixture of 4.82 grams of 3,5-dinitro-4-chloro-o-toluonitrile and 3 grams of di-n-propylamine in 25 ml. of toluene is refluxed 8 hours. The cooled mixture is then washed with water, dilute acid, and finally water. The organic layer is separated and dried over MgSO$_4$. Removal of the drying agent by filtration and concentration of the filtrate in vacuo leaves a residual oil which when crystallized gives the product with melting point 97° C. to 99° C.

N-sec-butyl-4-cyano-3-methyl-2,6-dinitroaniline is prepared by the above procedure substituting sec-butylamine for the di-n-propylamine. The desired product possessed a melting point of 102° C. to 103° C.

EXAMPLE 99

Preparation of (—)-N-sec-Butyl-2,6-dinitro-3,4-xylidine (—)-sec-Butylamine [prepared according to L. Verbit and P. J. Heffron, Journal of Organic Chemistry 32, 3199 (1967)] was reacted with 4-chloro-3,5-dinitro-o-xylene as by the general procedure of Example 5 to give a yellow-orange solid with melting point 37° C. to 38.5° C., $[\alpha]_D^{25°} = -51.38°$ (c 2.071, ethanol). Concentrations, abbreviated c herein, are measured in grams per 100 ml. of solution.

EXAMPLE 100

Preparation of (—)-N-[1-(Methoxymethyl)propyl]-2,6-dinitro-3,4-xylidine (—)-2-Amino-1-butanol [100 grams, prepared according to D. Pitre and E. B. Grabitz, Chimia 23, 399 (1969)] was added in a dropwise manner to a stirred solution of tert-butanol (800 ml.) containing potassium tert-butoxide (126 grams). After warming this mixture to 70° C. to 80° C. for 2 hours, methyl iodide (175 grams) was added slowly at temperatures below 50° C. The suspension which formed was then stirred with refluxing overnight. After removal of the solid phase by filtration, the filtrate was fractionally distilled to give (—)-1-methoxymethyl)propylamine contaminated with traces of tert-butanol, boiling point 125° C. to 147° C./760 mm. This amine was then allowed to react with 4-chloro-3,5-dinitro-o-xylene, as described earlier, to give the desired product as a bright yellow solid with melting point 42.5° C. to 44° C., $[\alpha]_D^{25°} = 137.6°$ (c 2.504, chloroform).

EXAMPLES 101 to 106

The following optical isomers were also prepared using the appropriate optically active amine and following essentially the procedure of Example 100 above:

TABLE VI

| Example Number | | Compound Name | Melting Point ° C. | $[\alpha]_D^{25°}$ |
|---|---|---|---|---|
| 101 | (+)- | N-sec-butyl-2,6-dinitro-3,4-xylidine | 38–38.5 | + 50.18 (c 2.217, ethanol) |
| 102 | (+)- | N-[1-(methoxymethyl)-propyl]-2,6-dinitro 3,4-xylidine | 43–44 | +132.2 (c 2.504, chloroform) |
| 103 | (—)- | N(1-methylbutyl)-2,6-dinitro-3,4-xylidine | 59–61 | − 58.0 (c 2.449, ethanol) |
| 104 | (—)- | N-sec-butyl-4-chloro-2,6-dinitro-m-toluidine | oil | − 42.3 (c 2.550, ethanol) |
| 105 | (—)- | 4-chloro-N-[1-methoxymethyl)-propyl]-2,6-dinitro-m-toluidine | 40–42 | −107 (c 2.466, CHCl$_3$) |
| 106 | (—)- | 4-chloro-N-(1-methylbutyl)- | oil | − 57.2 (c 3.263, ethanol) |

TABLE VI-continued

| Example Number | Compound Name | Melting Point °C. | $[\alpha]_D^{25°}$ |
|---|---|---|---|
| | 2,6-dinitro-m-toluidine | | |

EXAMPLES 107 to 178

The selective preemergence herbicidal activity of the compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous-acetone solution containing test compound in sufficient quantity to provide the equivalent of about 0.25 to 4 pounds per acre of test compound per cup. The treated cups are then placed on greenhouse benches, watered and cared for in accordance with conventional greenhouse procedures. Three of four weeks after treatment, the tests are terminated and each cup is examined and rated according to the rating system set forth below. The herbicidal proficiency of the active ingredients of the present invention is evident from the test results which are reported in the tables below.

Rating System

| Rating System | % Difference in Growth from the Check* |
|---|---|
| 0 - no effect | 0 |
| 1 - possible effect | 1–10 |
| 2 - slight effect | 11–25 |
| 3 - moderate effect | 26–40 |
| 5 - definite injury | 41–60 |
| 6 - herbicidal effect | 61–75 |
| 7 - good herbicidal effect | 76–90 |
| 8 - approaching complete kill | 91–99 |
| 9 - complete kill | 100 |
| 4 - abnormal growth, i.e., a definite physiological malformation but with an over-all effect less than a 5 on the rating scale. | |

*Based on visual determination of stand, size, vigor, chlorosis, growth malformation and over-all plant appearance.

Plant Abbreviations

| | | | |
|---|---|---|---|
| CR | - Crabgrass | BA | - Barnyard grass |
| VEL | - Velvet leaf | FOX | - Green foxtail |
| PI | - Pigweed | MG | - Annual Morning-glory |
| LA | - Lambsquarters | COT | - Cotton |
| COR | - Corn | SB | - Sugarbeets |
| WO | - Wild oats | SOY | - Soybean |

TABLE VII

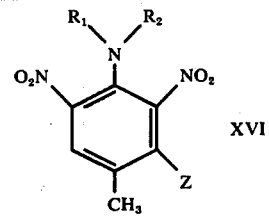

XVI

| Ex. No. | Z | R₁ | R₂ | Rate lb./acre | CR | VEL | PI | LA | COR | WO | BA | FOX | MG | COT | SB | SOY |
|---|---|---|---|---|---|---|---|---|---|---|---|---|---|---|---|---|
| 107 | CH₃ | CH₃ | CH₃ | 4 | 7 | 0 | 8 | 5 | 0 | 1 | 8 | 9 | 0 | 0 | 0 | 0 |
| | | | | 2 | 6 | 0 | 8 | 6 | 0 | 0 | 6 | 8 | 0 | 0 | 0 | 0 |
| 108 | CH₃ | CH₂CH=CH₂ | CH₂CH=CH₂ | 4 | 9 | 0 | 9 | 6 | 1 | 0 | 9 | 9 | 0 | 0 | 0 | 0 |
| | | | | 2 | 6 | 0 | 2 | 5 | 1 | 0 | 7 | 7 | 0 | 0 | 0 | 0 |
| | | | | 1 | 7 | 0 | 0 | 0 | 0 | 0 | 5 | 3 | 0 | 0 | 0 | 0 |
| 109 | CH₃ | CH₃ | ⌬ | 4 | 9 | 0 | 7 | 6 | 0 | 0 | 8 | 9 | 0 | 0 | 0 | 0 |
| | | | | 2 | 8 | 0 | 0 | 0 | 0 | 0 | 3 | 3 | 0 | 0 | 0 | 0 |
| | | | | 1 | 3 | 0 | 0 | 0 | 0 | 0 | 1 | 1 | 0 | 0 | 0 | 0 |
| 110 | CH₃ | H | CH₂CH=CH₂ | 4 | 9 | 0 | 8 | 7 | 3 | 0 | 9 | | 0 | 3 | 1 | 0 |
| | | | | 2 | 9 | 0 | 8 | 5 | 0 | 0 | 7 | | 0 | 0 | 0 | 0 |
| | | | | 1 | 8 | 0 | 5 | 5 | 0 | 0 | 6 | 5 | 0 | 0 | 0 | 0 |
| 111 | CH₃ | H | C₄H₉-i | 4 | 9 | 0 | 8 | 6 | 3 | 0 | 8 | | 0 | 0 | 2 | 0 |
| | | | | 2 | 9 | 1 | 6 | 0 | 0 | 2 | 5 | 8 | 0 | 0 | 0 | 0 |
| | | | | 1 | 7 | 0 | 0 | 0 | 0 | 0 | 3 | 5 | 0 | 0 | 0 | 0 |
| 112 | CH₃ | H | C₄H₉-tert | 4 | 7 | 0 | 7 | 8 | 0 | 0 | 6 | 7 | 0 | 0 | 2 | 0 |
| | | | | 2 | 6 | 0 | 3 | 2 | 1 | 0 | 2 | 5 | 0 | 0 | 1 | 2 |
| 113 | CH₃ | H | CH(CH₂CH₂CH₃)₂ | 4 | 9 | 6 | 9 | 8 | 0 | 0 | 7 | 9 | 2 | — | 7 | 3 |
| | | | | 2 | 9 | 2 | 8 | 8 | 0 | 0 | 7 | 8 | 0 | 0 | 8 | 0 |
| | | | | 1 | 8 | 0 | 8 | 6 | 0 | 0 | 5 | 7 | 0 | 0 | 7 | 0 |
| 114 | CH₃ | H | CH₃CH(CH₂)₄CH₃ | 4 | 2 | 0 | 0 | 0 | 0 | 0 | 0 | 3 | 0 | 0 | 3 | |

TABLE VII-continued
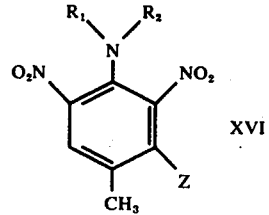
XVI
| Ex. No. | Z | R₁ | R₂ | Rate lb./acre | CR | VEL | PI | LA | COR | WO | BA | FOX | MG | COT | SB | SOY |
|---|---|---|---|---|---|---|---|---|---|---|---|---|---|---|---|---|
| 115 | CH₃ | H | C₂H₅CHCH₂CH₂CH₃ | 4 | 9 | 7 | 9 | 8 | 5 | 5 | 9 | 9 | 6 | 0 | 8 | 0 |
|  |  |  |  | 2 | 9 | 7 | 8 | 8 | 0 | 3 | 8 | 9 | 2 | 0 | 8 | 0 |
|  |  |  |  | 1 | 9 | 5 | 8 | 8 | 0 | 1 | 8 | 9 | 0 | 0 | 6 | 0 |
|  |  |  |  | ½ | 9 | 2 | 6 | 8 | 0 | 1 | 6 | 8 | 0 | 0 | 2 | 0 |
|  |  |  |  | ¼ | 8 | 0 | 5 | 7 | 0 | 0 | 5 | 6 | 0 | 0 | 0 | 0 |
| 116 | CH₃ | H | CH₂C(CH₃)₃ | 4 | 5 | 0 | 2 | 0 | 0 | 0 | 2 | 7 | 0 | 0 | 0 | 0 |
| 117 | CH₃ | C₂H₅ | C₂H₅ | 4 | 9 | 0 | 8 | 7 | 2 | 5 | 9 | 9 | 0 | 0 | 0 | 0 |
|  |  |  |  | 2 | 9 | 0 | 8 | 3 | 3 | 2 | 9 | 9 | 0 | 1 | 3 | 0 |
|  |  |  |  | 1 | 9 | 0 | 7 | 3 | 0 | 1 | 9 | 9 | 0 | 0 | 0 | 0 |
| 118 | CH₃ | H | C₄H₉-n | 4 | 9 | 0 | 7 | 6 | 3 | 1 | 8 | 9 | 1 | 0 | 0 |  |
|  |  |  |  | 2 | 7 | 0 | 0 | 0 | 0 | 0 | 1 | 9 | 1 | 0 | 0 | 0 |
|  |  |  |  | 1 | 7 | 0 | 0 | 0 | 0 | 0 | 0 | 9 | 0 | 0 | 0 | 0 |
| 119 | CH₃ | H | CH₃CH—CH₂CH₃ | 4 | 9 | 8 | 8 | 8 | 3 | 2 | 9 | 9 | 2 | 0 | 8 | 3 |
|  |  |  |  | 2 | 9 | 8 | 8 | 8 | 3 | 0 | 9 | 9 | 0 | 0 | 8 | 0 |
|  |  |  |  | 1 | 9 | 5 | 7 | 8 | 0 | 0 | 9 | 9 | 0 | 0 | 7 | 0 |
|  |  |  |  | ½ | 9 | 0 | 3 | 7 | 0 | 0 | 7 | 9 | 0 | 0 | 0 | 0 |
|  |  |  |  | ¼ | 8 | 0 | 0 | 5 | 0 | 0 | 5 | 5 | 0 | 0 | 0 | 0 |
| 120 | CH₃ | C₄H₉-n | C₄H₉-n | 4 | 8 | 1 | 5 | 2 | 2 | 0 | 2 | 8 | 0 | 7 | 0 | 0 |
|  |  |  |  | 2 | 8 | 0 | 1 | 0 | 0 | 0 | 1 | 5 | 0 | 1 | 2 | 0 |
| 121 | CH₃ | H | C₃H₇-i | 4 | 9 | 3 | 9 | 8 | 0 | 2 | 9 | 9 | 0 | 0 | 7 | 0 |
|  |  |  |  | 2 | 9 | 1 | 8 | 8 | 1 | 1 | 9 | 9 | 0 | 0 | 5 | 0 |
|  |  |  |  | 1 | 9 | 1 | 7 | 7 | 0 | 0 | 9 | 9 | 0 | 0 | 0 | 0 |
|  |  |  |  | ½ | 9 | 0 | 2 | 2 | 1 | 0 | 7 | 9 | 0 | 0 | 0 | 0 |
| 122 | CH₃ | C₃H₇-n | C₃H₇-n | 4 | 9 | 3 | 9 | 7 | 0 | 2 | 9 | 9 | 4 | 1 | 0 | 0 |
|  |  |  |  | 2 | 9 | 1 | 9 | 7 | 0 | 0 | 8 | 9 | 0 | 0 | 0 | 0 |
|  |  |  |  | 1 | 9 | 0 | 8 | 3 | 0 | 0 | 7 | 9 | 0 | 0 | 0 | 0 |
|  |  |  |  | ½ | 8 | 0 | 6 | 2 | 0 | 0 | 5 | 9 | 0 | 0 | 0 | 0 |
| 123 | CH₃ | C₂H₅ | C₄H₉-n | 4 | 9 | 0 | 9 | 7 | 0 | 0 | 9 | 9 | 0 | 0 | 0 | 0 |
|  |  |  |  | 2 | 8 | 0 | 8 | 6 | 1 | 0 | 8 | 9 | 0 | 0 | 0 | 0 |
|  |  |  |  | 1 | 3 | 0 | 6 | 1 | 0 | 0 | 6 | 8 | 0 | 0 | 0 | 0 |
|  |  |  |  | ½ | 3 | 0 | 2 | 0 | 0 | 0 | 1 | 6 | 0 | 0 | 0 | 0 |
| 124 | CH₃ | H | C₃H₇-n | 4 | 9 | 0 | 8 | 8 | 0 | 7 | 9 | 3 | 0 | 0 | 0 | 2 |
|  |  |  |  | 2 | 9 | 0 | 8 | 7 | 0 | 2 | 8 | 8 | 0 | 0 | 0 | 0 |
|  |  |  |  | 1 | 9 | 0 | 7 | 1 | 0 | 0 | 6 | 8 | 0 | 0 | 0 | 0 |
| 125 | CH₃ |  | ⟨O⟩ | 4 | 7 | 0 | 8 | 7 | 0 | 0 | 9 | 5 | 0 | 0 | 0 | 0 |
|  |  |  |  | 2 | 2 | 0 | 7 | 0 | 0 | 0 | 6 | 3 | 0 | 0 | 0 | 0 |
|  |  |  |  | 1 | 1 | 0 | 0 | 0 | 0 | 0 | 3 | 0 | 0 | 5 | 0 | 0 |
| 126 | CH₃ | H | CH₃CHCH₂CH(CH₃)₂ | 4 | 9 | 3 | 8 | 7 | 0 | 0 | 9 | 9 | 0 | 0 | 1 | 0 |
|  |  |  |  | 2 | 9 | 2 | 7 | 7 | 0 | 0 | 8 | 9 | 2 | 0 | 1 | 2 |
|  |  |  |  | 1 | 9 | 0 | 7 | 7 | 0 | 0 | 6 | 9 | 0 | 5 | 1 | 5 |
|  |  |  |  | ½ | 8 | 0 | 6 | 6 | 0 | 0 | 3 | 7 | 0 | 0 | 0 | 0 |
|  |  |  |  | ¼ | 6 | 0 | 2 | 5 | 0 | 0 | 0 | 0 | 0 | 0 | 0 | 0 |
| 127 | CH₃ | C₂H₅ | C₃H₇-n | 4 | 9 | 0 | 6 | 7 | 0 | 2 | 9 | 9 | 0 | 0 | 0 | 0 |
|  |  |  |  | 2 | 9 | 0 | 0 | 7 | 0 | 2 | 9 | 9 | 0 | 0 | 0 | 0 |
|  |  |  |  | 1 | 8 | 0 | 0 | 3 | 0 | 0 | 6 | 9 | 0 | 0 | 0 | 0 |
|  |  |  |  | ½ | 6 | 0 | 0 | 0 | 0 | 0 | 0 | 7 | 0 | 0 | 0 | 0 |
|  |  |  |  | ¼ | 2 | 2 | 0 | 2 | 0 | 0 | 2 | 8 | 0 | 0 | 0 | 0 |
| 128 | CH₃ | H | C₂H₅CHC₂H₅ | 4 | 9 | 7 | 8 | 8 | 7 | 5 | 9 | 9 | 7 | 5 | 5 | 3 |
|  |  |  |  | 2 | 9 | 7 | 8 | 8 | 6 | 2 | 9 | 9 | 7 | 2 | 5 | 2 |
|  |  |  |  | 1 | 9 | 6 | 7 | 8 | 2 | 0 | 7 | 9 | 6 | 1 | 2 | 0 |
|  |  |  |  | ½ | 9 | 5 | 6 | 8 | 1 | 0 | 8 | 9 | 3 | 0 | 1 | 0 |
|  |  |  |  | ¼ | 9 | 5 | 6 | 7 | — | 0 | 5 | 9 | 1 | 0 | 0 | 0 |
| 129 | CH₃ | H | CH₃CHC₃H₇ | 4 | 9 | 7 | 8 | 8 | 8 | 3 | 9 | 9 | 5 | 0 | 6 | 0 |
|  |  |  |  | 2 | 9 | 2 | 8 | 8 | 2 | 2 | 9 | 9 | 6 | 0 | 5 | 0 |
|  |  |  |  | 1 | 9 | 2 | 8 | 8 | 0 | 0 | 8 | 9 | 5 | 9 | 2 | 0 |
|  |  |  |  | ½ | 9 | 0 | 5 | 7 | 0 | 0 | 3 | 8 | 2 | 0 | 0 | 0 |
|  |  |  |  | ¼ | 9 | 1 | 2 | 6 | 0 | 0 | 2 | 5 | 0 | 0 | 0 | 0 |
| 130 | CH₃ | H | CH₂CH₂CH(CH₃)₂ | 4 | 9 | 0 | 6 | 6 | 0 | 0 | 6 | 5 | 0 | 0 | 0 | 0 |
|  |  |  |  | 2 | 7 | 0 | 0 | 2 | 0 | 0 | 3 | 3 | 0 | 0 | 0 | 0 |

TABLE VII-continued

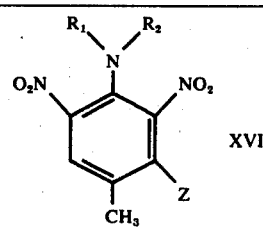

| Ex. No. | Z | R₁ | R₂ | Rate lb./acre | CR | VEL | PI | LA | COR | WO | BA | FOX | MG | COT | SB | SOY |
|---|---|---|---|---|---|---|---|---|---|---|---|---|---|---|---|---|
| 131 | $CH_3$ | | cyclohexyl | 4 | 9 | 1 | 5 | 7 | 7 | 0 | 6 | 8 | 2 | 0 | 0 | 0 |
| | | | | 2 | 8 | 0 | 2 | 6 | 2 | 0 | 2 | 7 | 0 | 0 | 0 | 0 |
| | | | | 1 | 7 | 0 | 0 | 2 | 3 | 0 | 0 | 5 | 0 | 0 | 0 | 0 |
| 132 | $CH_3$ | | cyclopentyl | 4 | 9 | 2 | 5 | 8 | 0 | 0 | 9 | 9 | 2 | 0 | 0 | 1 |
| | | | | 2 | 9 | 0 | 3 | 7 | 0 | 0 | 5 | 8 | 0 | 0 | 0 | 0 |
| | | | | 1 | 7 | 0 | 0 | 3 | 0 | 0 | 2 | 7 | 0 | 0 | 0 | 0 |
| 133 | $CH_3$ | H | $CH_3CHCH(CH_3)_2$ | 4 | 9 | 7 | 8 | 8 | 1 | 3 | 8 | 9 | 3 | 0 | 6 | 0 |
| | | | | 2 | 9 | 5 | 7 | 8 | 0 | 0 | 7 | 9 | 2 | 0 | 3 | 0 |
| | | | | 1 | 9 | 3 | 6 | 8 | 0 | 0 | 3 | 7 | 0 | 0 | 1 | 0 |
| | | | | ½ | 8 | 0 | 2 | 7 | — | 0 | 2 | 5 | 0 | 1 | 0 | 0 |
| | | | | ¼ | 7 | 0 | 2 | 3 | 1 | 0 | 1 | 1 | 0 | 0 | 0 | 0 |
| 134 | $CH_3$ | H | $CH_3CHCH_2CH_2CH(CH_3)_2$ | 4 | 5 | 0 | 0 | 0 | 0 | 0 | 0 | 2 | 0 | 0 | 0 | 0 |
| 135 | $CH_3$ | H | $CH_3CHC_4H_9$-t | 4 | 5 | 0 | 2 | 0 | 0 | 8 | 3 | 0 | 0 | 0 | 0 | 0 |
| | | | | 2 | 3 | 0 | 0 | 0 | 0 | 0 | 0 | 0 | 0 | 0 | 0 | 0 |
| 136 | $CH_3$ | | 2,6-dimethyltetrahydropyranyl | 4 | 9 | 0 | 0 | 0 | 0 | 0 | 8 | 8 | 3 | 0 | 2 | 0 |
| | | | | 2 | 8 | 0 | 0 | 0 | 0 | 0 | 5 | 7 | 3 | 0 | 0 | 0 |
| | | | | 1 | 6 | 0 | 0 | 0 | 0 | 0 | 0 | 2 | 3 | 0 | 0 | 0 |
| 137 | $CH_3$ | H | $C_4H_9CHCH_3$ | 4 | 9 | 2 | 7 | 8 | 0 | 1 | 8 | 9 | 0 | 0 | 2 | 0 |
| | | | | 2 | 9 | 0 | 5 | 6 | 0 | 0 | 7 | 8 | 0 | 0 | 0 | 0 |
| | | | | 1 | 8 | 0 | 3 | 3 | 0 | 0 | 5 | 6 | 0 | 0 | 0 | 0 |
| | | | | ½ | 7 | 0 | 0 | 2 | 0 | 0 | 0 | 0 | 0 | 0 | 0 | 0 |

TABLE VIII

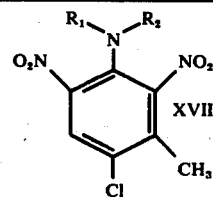

| Ex. No. | R₁ | R₂ | RaTE lb./acre | CR | VEL | PI | LA | COR | WO | BA | FOX | MG | COT | SB | SOY |
|---|---|---|---|---|---|---|---|---|---|---|---|---|---|---|---|
| 138 | H | $C_3H_7$-n | 4 | 9 | 0 | 8 | 8 | 3 | 0 | 8 | 8 | 0 | 0 | 3 | 0 |
| | | | 2 | 9 | 0 | 7 | 7 | 0 | 0 | 6 | 6 | 0 | 0 | 0 | 0 |
| | | | 1 | 5 | 0 | 6 | 3 | 5 | 0 | 3 | 3 | 0 | 0 | 0 | 0 |
| 139 | $C_3H_7$-n | $C_3H_7$-n | 4 | 9 | 3 | 8 | 8 | 0 | 0 | 9 | 9 | 0 | 0 | 1 | 1 |
| | | | 2 | 9 | 0 | 7 | 7 | 0 | 0 | 8 | 9 | 0 | 0 | 0 | 0 |
| | | | 1 | 9 | 0 | 7 | 6 | 0 | 0 | 6 | 8 | 0 | 0 | 0 | 0 |
| 140 | H | $C_6H_{13}$-n | 2 | 3 | | | | | | 0 | 0 | | | | |
| | | | 1 | 3 | | | | | | 0 | 0 | | | | |
| 141 | H | $CH_2CH=CH_2$ | 2 | 8 | | | | | | 1 | 7 | | | | |
| 142 | H | $C_3H_7$-i | 2 | 9 | | | | | | 8 | 9 | | | | |
| | | | 1 | 8 | | | | | | 7 | 6 | | | | |
| | | | ½ | 5 | | | | | | 3 | 3 | | | | |
| 143 | $CH_2CH=CH_2$ | $CH_2CH=CH_2$ | 2 | 9 | | | | | | 8 | 9 | | | | |
| | | | 1 | 7 | | | | | | 6 | 5 | | | | |
| | | | ½ | 6 | | | | | | 5 | 2 | | | | |
| | | | ¼ | 6 | | | | | | 3 | 3 | | | | |
| 144 | H | $CH_3CHC_2H_5$ | 2 | 9 | | | | | | 9 | 9 | | | | |
| | | | 1 | 9 | | | | | | 8 | 9 | | | | |
| | | | ½ | 9 | | | | | | 7 | 7 | | | | |
| | | | ¼ | 8 | | | | | | 6 | 8 | | | | |
| 145 | $C_2H_5$ | $C_2H_5$ | 2 | 9 | | | | | | 9 | 9 | | | | |
| | | | 1 | 8 | | | | | | 8 | 7 | | | | |
| | | | ½ | 3 | | | | | | 5 | 6 | | | | |
| | | | ¼ | 0 | | | | | | 3 | 1 | | | | |

TABLE VIII-continued
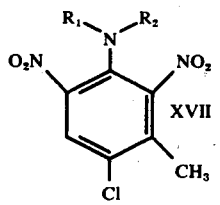
| Ex. No. | $R_1$ | $R_2$ | RaTE lb./acre | CR | VEL | PI | LA | COR | WO | BA | FOX | MG | COT | SB | SOY |
|---|---|---|---|---|---|---|---|---|---|---|---|---|---|---|---|
| 146 | | (tetrahydropyran) | 4 | 5 | 1 | 0 | 5 | 5 | 0 | 0 | 0 | 3 | 0 | 0 | 0 |
| 147 | H | $CH_3CHCH_2CH(CH_3)_2$ | 4 | 9 | 3 | 9 | 7 | 0 | 0 | 7 | 9 | 3 | 0 | 5 | 1 |
| | | | 2 | 9 | 2 | 8 | 6 | 0 | 0 | 3 | 9 | 2 | 0 | 3 | 0 |
| | | | 1 | 9 | 0 | 8 | 6 | 0 | 0 | 5 | 8 | 0 | 0 | 1 | 0 |
| 148 | H | (cyclohexyl) | 4 | 9 | 0 | 5 | 2 | 0 | 0 | 2 | 3 | 2 | 0 | 0 | 1 |
| | | | 2 | 7 | 1 | 1 | 1 | 0 | 0 | 1 | 2 | 5 | 0 | 0 | 1 |
| 149 | H | $C(CH_3)_3$ | 4 | 5 | 2 | 2 | 0 | 0 | 0 | 0 | 3 | 0 | 0 | 1 | 0 |
| | | | 2 | 2 | 0 | 0 | 0 | 0 | 0 | 0 | 0 | 0 | 0 | 1 | 0 |
| 150 | H | $CH_2CH(CH_3)_2$ | 4 | 8 | 2 | 3 | 0 | 0 | 0 | 6 | 7 | 0 | 0 | 0 | 0 |
| | | | 2 | 6 | 0 | 0 | 0 | 0 | 0 | 3 | 5 | 0 | 0 | 0 | 0 |
| 151 | H | $C_2H_5CHC_2H_5$ | 4 | 9 | 7 | 9 | 8 | 0 | 2 | 9 | 9 | 5 | 0 | 8 | 0 |
| | | | 2 | 9 | 6 | 8 | 7 | 0 | 2 | 7 | 9 | 5 | 0 | 7 | 0 |
| | | | 1 | 9 | 5 | 7 | 7 | 0 | 1 | 5 | 9 | 6 | 0 | 6 | 0 |
| | | | ½ | 9 | 3 | 6 | 6 | 0 | 0 | 1 | 9 | 2 | 0 | 3 | 0 |
| | | | ¼ | 7 | 0 | 2 | 5 | 0 | 0 | 2 | 5 | 0 | 0 | 0 | 0 |
| 152 | $CH_3$ | $CH_3$ | 4 | 3 | 0 | 0 | 5 | 0 | 1 | 2 | 5 | 0 | 0 | 0 | 0 |
| 153 | H | $CH_3CHC_3H_7$-n | 4 | 9 | 6 | 8 | 8 | 3 | 0 | 9 | 9 | 0 | 0 | 8 | 0 |
| | | | 2 | 9 | 5 | 8 | 8 | 2 | 0 | 7 | 9 | 0 | 0 | 7 | 0 |
| | | | 1 | 9 | 2 | 7 | 7 | 0 | 0 | 7 | 7 | 0 | 0 | 5 | 0 |
| | | | ½ | 8 | 2 | 5 | 5 | 0 | 0 | 6 | 6 | 0 | 0 | 2 | 0 |
| | | | ¼ | 8 | 0 | 0 | 0 | 0 | 0 | 3 | 2 | 0 | 0 | 0 | 0 |
TABLE IX
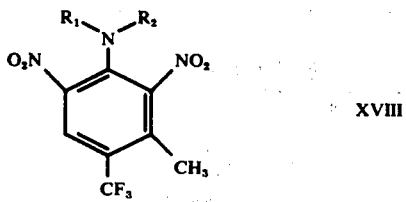
| Ex. No. | $R_1$ | $R_2$ | Rate lb./acre | CR | VEL | PI | LA | COR | WO | BA | FOX | MG | COT | SB | SOY |
|---|---|---|---|---|---|---|---|---|---|---|---|---|---|---|---|
| 154 | $C_3H_7$-n | $C_3H_7$-n | 4 | 9 | 3 | 8 | 7 | 3 | 2 | 9 | 9 | 3 | 0 | 0 | 3 |
| | | | 2 | 9 | 0 | 8 | 6 | 2 | 3 | 8 | 9 | 0 | 0 | 0 | 3 |
| | | | 1 | 9 | 0 | 6 | 6 | 0 | 2 | 8 | 9 | 0 | 0 | 0 | 0 |
| | | | ½ | 7 | 0 | 3 | 3 | 0 | 2 | 6 | 7 | 0 | 0 | 0 | 0 |
| 155 | H | $CH_3CHC_2H_5$ | 4 | 9 | 7 | 8 | 8 | 5 | 3 | 9 | 9 | 7 | 5 | 7 | 7 |
| | | | 2 | 9 | 7 | 8 | 8 | 5 | 2 | 9 | 9 | 7 | 0 | 6 | 5 |
| | | | 1 | 9 | 6 | 7 | 7 | 3 | 2 | 9 | 9 | 6 | 0 | 5 | 2 |
| | | | ½ | 9 | 2 | 6 | 7 | 0 | 0 | 8 | 9 | 0 | 0 | 3 | 0 |
| | | | ¼ | 7 | 2 | 3 | 5 | 0 | 0 | 7 | 7 | 0 | 0 | 2 | 0 |
| 156 | H | $C_3H_7$-i | 4 | 9 | 5 | 7 | 7 | 0 | 1 | 9 | 9 | 0 | 0 | 3 | 0 |
| | | | 2 | 9 | 0 | 6 | 6 | 0 | 0 | 8 | 9 | 0 | 0 | 0 | 0 |
| | | | 1 | 9 | 0 | 3 | 0 | 0 | 0 | 7 | 8 | 0 | 0 | 1 | 0 |
| | | | ½ | 7 | 0 | 0 | 1 | 0 | 0 | 3 | 6 | 0 | 0 | 0 | 0 |
| 157 | $CH_3$ | $CH_3$ | 4 | 3 | 0 | 0 | 2 | 6 | 0 | 3 | 3 | 0 | 0 | 0 | 0 |
| 158 | $C_2H_5$ | $C_2H_5$ | 4 | 9 | 0 | 8 | 7 | 2 | 3 | 9 | 9 | 2 | 0 | 3 | 0 |
| | | | 2 | 9 | 0 | 7 | 5 | 1 | 0 | 8 | 9 | 2 | 0 | 2 | 0 |
| | | | 1 | 8 | 0 | 3 | 2 | 0 | 0 | 8 | 8 | 1 | 0 | 1 | 0 |
| | | | ½ | 7 | 0 | 0 | 0 | 0 | 0 | 6 | 5 | 3 | 0 | 0 | 0 |
| 159 | H | $C_2H_5CHC_2H_5$ | 4 | 9 | 8 | 9 | 9 | 5 | 5 | 9 | 9 | 7 | 7 | 8 | 7 |
| | | | 2 | 9 | 8 | 8 | 8 | 3 | 3 | 9 | 9 | 7 | 5 | 9 | 7 |
| | | | 1 | 9 | 7 | 8 | 8 | 3 | 2 | 9 | 9 | 6 | — | 7 | 5 |
| | | | ½ | 9 | 5 | 7 | 8 | 0 | 1 | 8 | 9 | 5 | 0 | 5 | 0 |
| | | | ¼ | 9 | 5 | 7 | 7 | 0 | 0 | 7 | 8 | 2 | 0 | 2 | 0 |

TABLE X

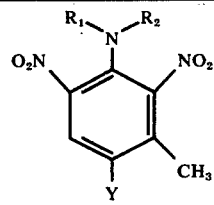

XIX

| Ex. No. | Y | R₁ | R₂ | Rate lb./acre | CR | VEL | PI | LA | COR | WO | BA | FOX | MG | COT | SB | SOY |
|---|---|---|---|---|---|---|---|---|---|---|---|---|---|---|---|---|
| 160 | SO₂NH₂ | H | C₄H₉-sec | 4 | 9 | 8 | 9 | — | 0 | 0 | 7 | 9 | 6 | 7 | 7 | 7 |
| | | | | 2 | 9 | 8 | 9 | 8 | 0 | 0 | 2 | 9 | 3 | 5 | 9 | 5 |
| | | | | 1 | 8 | 7 | 8 | 8 | 0 | 1 | 0 | 7 | 0 | 2 | 8 | 1 |
| | | | | ½ | 7 | 8 | 6 | 5 | 0 | 1 | 0 | 3 | 0 | 0 | 2 | 3 |
| 161 | SO₂NH₂ | C₃H₇-n | C₃H₇-n | 4 | 9 | 7 | 9 | 8 | 0 | 1 | 5 | 9 | 5 | 7 | 8 | 0 |
| | | | | 2 | 9 | 5 | 8 | 9 | 0 | 0 | 8 | 9 | 3 | 0 | 3 | 0 |
| | | | | 1 | 7 | 5 | 7 | 8 | 0 | 1 | 2 | 9 | 2 | 0 | 5 | 0 |
| | | | | ½ | 5 | 6 | 3 | 7 | 0 | 0 | 2 | 6 | 0 | 0 | 0 | 0 |
| 162 | SO₂NHCH₃ | C₃H₇-n | C₃H₇-n | 4 | 9 | 1 | 0 | 8 | 0 | 0 | 8 | 9 | 3 | 0 | 5 | 0 |
| | | | | 2 | 9 | 1 | 6 | 6 | 0 | 0 | 6 | 8 | 1 | 0 | 6 | 0 |
| | | | | 1 | 8 | 0 | 5 | 7 | 0 | 0 | 3 | 6 | 0 | 0 | 0 | 0 |
| | | | | ½ | 7 | 0 | 3 | 3 | 0 | 0 | 3 | 5 | 0 | 0 | 0 | 0 |
| 163 | SO₂N(CH₂)₂ | C₃H₇-n | C₃H₇-n | 4 | 9 | 0 | 5 | 2 | 0 | 0 | 0 | 6 | 0 | 0 | 0 | 0 |
| | | | | 2 | 7 | 0 | 3 | 2 | 0 | 0 | 0 | 5 | 0 | 0 | 0 | 0 |
| | | | | 1 | 7 | 0 | 3 | 0 | 0 | 0 | 0 | 3 | 0 | 0 | 0 | 0 |
| | | | | ½ | 3 | 0 | 2 | 0 | 0 | 0 | 0 | 1 | 0 | 0 | 0 | 0 |
| 164 | SO₂NHCH—CH₃ \| C₂H₅ | C₃H₇-n | C₃H₇-n | 4 | 6 | 1 | | | | | | | | | | |
| | | | | 2 | 2 | | | | | | | | | | | |
| 165 | SO₂NHCH₃ | H | C₄H₉-sec | 4 | 9 | 7 | 9 | 9 | 0 | 3 | 9 | 9 | 7 | 2 | 8 | 2 |
| | | | | 2 | 9 | 7 | 8 | 9 | 0 | 3 | 7 | 9 | 7 | 0 | 7 | 2 |
| | | | | 1 | 9 | 5 | 8 | 8 | 0 | 0 | 7 | 8 | 3 | 2 | 6 | 2 |
| | | | | ½ | 9 | 3 | 7 | 7 | 0 | 0 | 5 | 8 | 0 | 0 | 7 | 0 |
| 166 | SO₂NHCH₃ | H | CH₃ | 4 | 5 | | 3 | 5 | | | | | | | | |
| | | | | 2 | | | | 2 | | | | | | | | |
| 167 | SO₂N(CH₃)₂ | H | C₄H₉-sec | 4 | 9 | 5 | 6 | 8 | 5 | 0 | 6 | 9 | 2 | 0 | 6 | 0 |
| | | | | 2 | 9 | 3 | 7 | 8 | 0 | 0 | 5 | 9 | 0 | 0 | 6 | 0 |
| | | | | 1 | 9 | 0 | 3 | 6 | 0 | 0 | 2 | 6 | 0 | 0 | 0 | 0 |
| | | | | ½ | 9 | 0 | 5 | 5 | 0 | 0 | 0 | 6 | 0 | 0 | 0 | 0 |
| | | | | ¼ | 6 | 0 | 0 | 0 | 0 | 0 | 0 | 0 | 0 | 0 | 0 | 0 |
| 168 | SO₂NHC₄H₉-sec | H | C₄H₉-sec | 4 | 7 | | 3 | 6 | | | 1 | 5 | | | | |
| | | | | 2 | 3 | | 2 | | | | | 2 | | | | |
| 169 | CN | C₃H₇-n | C₃H₇-n | 4 | 9 | 7 | 8 | 8 | 0 | 3 | 9 | 9 | 3 | 0 | 8 | — |
| | | | | 2 | 9 | 6 | 7 | 8 | 3 | 0 | 7 | 9 | 0 | 0 | 7 | 0 |
| | | | | 1 | 9 | 5 | 6 | 6 | 0 | 0 | 7 | 8 | 0 | 2 | 6 | 2 |
| | | | | ½ | 7 | 3 | 2 | 5 | 0 | 0 | 6 | 5 | 0 | 0 | 5 | 0 |
| | | | | ¼ | 5 | 0 | 0 | 2 | 0 | 0 | 3 | 2 | 0 | 0 | 1 | 0 |
| 170 | CN | H | CH(C₂H₅)(CH₃) | 4 | 9 | 7 | 8 | 8 | 5 | 3 | 9 | 9 | 2 | 6 | 7 | 6 |
| | | | | 2 | 9 | 5 | 7 | 7 | 5 | 3 | 8 | 9 | 3 | 5 | 6 | 2 |
| | | | | 1 | 9 | 3 | 6 | 5 | 0 | 0 | 6 | 9 | 0 | 2 | 5 | 2 |
| | | | | ½ | 9 | 2 | 2 | 2 | 0 | 1 | 5 | 8 | 0 | 2 | 3 | 1 |
| | | | | ¼ | 3 | 0 | 3 | 0 | 0 | 0 | 2 | 3 | 0 | 0 | 0 | 0 |

TABLE XI

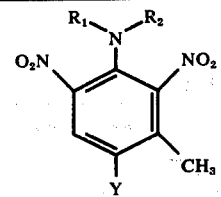

XX

| Ex. No. | Y | Z | R₁ | R₂ | Rate lb./acre | CR | VEL | PI | LA | COP | WO | BA | FOX | MG | COT | SB | SOY |
|---|---|---|---|---|---|---|---|---|---|---|---|---|---|---|---|---|---|
| 171 | CH₃ | CH₃ | H | —CHCH₂OCH₃ \| CH₃ | 4 | 9 | 7 | 9 | 9 | 0 | 5 | 9 | 9 | 5 | 0 | 8 | 5 |
| | | | | | 2 | 9 | 6 | 8 | 8 | 0 | 0 | 8 | 9 | 3 | 0 | 8 | 0 |
| | | | | | 1 | 9 | 3 | 7 | 8 | 0 | 0 | 8 | 7 | 0 | 0 | 6 | 0 |
| 172 | CH₃ | CH₃ | CH₃ | CH₂CH₂Cl | 4 | 9 | 0 | 6 | 7 | 0 | 0 | 8 | 8 | 1 | 0 | 6 | 0 |
| | | | | | 2 | 9 | 0 | 3 | 3 | 0 | 0 | 7 | 7 | 0 | 0 | 3 | 0 |
| 173 | CH₃ | CH₃ | H | CH₂CH(OCH₃)₂ | 4 | 9 | 0 | 5 | 7 | 0 | 0 | 8 | 7 | 5 | 0 | 3 | 0 |
| | | | | | 2 | 8 | 0 | 3 | 5 | 0 | 0 | 6 | 3 | 3 | 0 | 0 | 0 |
| | | | | | 1 | 7 | 0 | 0 | 3 | 0 | 0 | 2 | 0 | 0 | 0 | 0 | 0 |
| 174 | CH₃ | CH₃ | H | CH(C₂H₅)CH₂OCH₃ | 4 | 9 | 7 | 9 | 8 | 5 | 5 | 9 | 9 | 7 | 0 | 8 | 0 |
| | | | | | 2 | 9 | 7 | 8 | 8 | 0 | 3 | 9 | 9 | 3 | 0 | 6 | 0 |
| | | | | | 1 | 9 | 2 | 8 | 8 | 0 | 0 | 9 | 9 | 0 | 0 | 6 | 0 |
| 175 | CH₃ | CH₃ | H | CH₃(CH₃)CH₂Cl | 4 | 9 | 2 | 5 | 8 | 0 | 0 | 8 | 9 | 0 | 0 | 6 | 0 |
| | | | | | 2 | 9 | 0 | 3 | 8 | 0 | 0 | 7 | 9 | 0 | 0 | 0 | 0 |
| | | | | | 1 | 9 | 0 | 0 | 7 | 0 | 0 | 3 | 9 | 0 | 0 | 0 | 0 |
| 176 | CH₃ | CH₃ | H | CH(C₂H₅)CH₂Cl | 4 | 9 | 7 | 7 | 8 | 3 | 3 | 9 | 9 | 3 | 0 | 7 | 0 |
| | | | | | 2 | 9 | 7 | 7 | 8 | 0 | 0 | 8 | 9 | 0 | 0 | 7 | 0 |
| | | | | | 1 | 9 | 3 | 3 | 8 | 0 | 0 | 8 | 9 | 0 | 0 | 5 | 0 |
| 177 | CH₃ | CH₃ | H | CH₂CH₂CH₂OCH₃ | 4 | 9 | 1 | 5 | 3 | 0 | 0 | 5 | 3 | 2 | 0 | 0 | 0 |
| | | | | | 2 | 7 | 0 | 0 | 2 | 0 | 0 | 2 | 0 | 1 | 0 | 0 | 0 |
| 178 | Cl | CH₃ | H | CH₂CH₂CH₂OCH₃ | 4 | 9 | 6 | 8 | 8 | 0 | 0 | 8 | 8 | 2 | 0 | 7 | 3 |

TABLE XI-continued

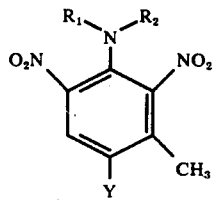

XX

| Ex. No. | Y | Z | R₁ | R₂ | Rate lb./acre | CR | VEL | PI | LA | COP | WO | BA | FOX | MG | COT | SB | SOY |
|---|---|---|---|---|---|---|---|---|---|---|---|---|---|---|---|---|---|
| | | | | | 2 | 9 | 7 | 7 | 8 | 0 | 0 | 7 | 6 | 0 | 0 | 7 | 2 |
| | | | | | 1 | 9 | 3 | 6 | 8 | 0 | 0 | 7 | 2 | 0 | 0 | 5 | 0 |

EXAMPLES 179 to 188

The herbicidal activity of various compounds of the present invention are demonstrated by the following tests, wherein seeds of monocotyledonous and dicotyledonous plants are planted in the top half-inch of soil in small plastic pots and sprayed with a solution of test compound. All spray applications are made to a dry soil surface through nozzles designed to deliver 86 gallons per acre of spray solution. Immediately after treatment, the pots are labeled, moved to a greenhouse, and watered. Three weeks after treatment, the herbicide activity is recorded using the Herbicidal Activity rating system reported below.

From the data reported in the table below, it can be seen that (1) the racemic compounds are highly active herbicidal agents; (2) the dextrorotatory (+) isomers are less active than the racemic compounds, but still effective as herbicidal agents at higher rates of application; and (3) the levorotatory (−) isomers are much more effective as herbicidal agents than either the corresponding racemic compound or the corresponding dextrorotatory (+) isomer.

Species List

| Code | Common Name | Scientific Name |
|---|---|---|
| LA | Lambsquarters | Chenopodium album |
| PI | Pigweed | Amaranthus retroflexus |

Species List-continued

| Code | Common Name | Scientific Name |
|---|---|---|
| MG | Morning-glory | Ipomoea hederacea |
| BA | Barnyard grass | Echinochloa crusgalli |
| CR | Crab grass | Digitairia sanguinalis |
| FO | Green foxtail | Setaria viridis |
| WO | Wild oat | Avena fatua |
| CN | Corn | Zea mays |
| CO | Cotton | Gossypium hirsutum |
| SY | Soybean | Glycine max |
| SB | Sugar beet | Beta vulgaris |
| VL | Velvet leaf | Abutilon theophrasti |

Herbicidal Activity Index

| Rating Scale | Observation | *% Difference in Growth from Checks |
|---|---|---|
| 9 | Complete kill | 100 |
| 8 | Approaching complete kill | 91–99 |
| 7 | Good herbicidal effect | 76–90 |
| 6 | Herbicidal effect | 61–75 |
| 5 | Definite injury | 41–60 |
| 4 | (See Below) | — |
| 3 | Moderate effect | 26–40 |
| 2 | Slight effect | 11–25 |
| 1 | Possible effect | 1–10 |
| 0 | No effect | 0 |

4 - Reserved for abnormal plant growth, i.e. a definite physiological malformation but with an over-all effect of less than 5 on the rating scale.
*Based on visual determination of stand, size, vigor, chlorosis.

TABLE XII

Herbicidal Activity of Optically Active and Racemic Dinitroaniline Compounds

| Ex. No. | Compound | Rate lb./Acre | LA | PI | MG | BA | CR | PO | WO | CN | CO | SY | SB | VL |
|---|---|---|---|---|---|---|---|---|---|---|---|---|---|---|
| 179 | (structure with NH—CH(C₂H₅)—CH₂—OCH₃, dinitro, dimethyl) (−) | 4 | 8 | 9 | 8 | 9 | 9 | 9 | 0 | 5 | 0 | — | 8 | 8 |
|  |  | 2 | 8 | 9 | 6 | 9 | 9 | 9 | 0 | 5 | 0 | 2 | 8 | 8 |
|  |  | 1 | 8 | 8 | 3 | 9 | 9 | 9 | 0 | 0 | 0 | 0 | 6 | 7 |
|  |  | 1/2 | 8 | 7 | 0 | 8 | 9 | 9 | 0 | 0 | 0 | 0 | 0 | 2 |
|  |  | 1/4 | 7 | 3 | 0 | 6 | 9 | 7 | 0 | 0 | 0 | 0 | 0 | 0 |
|  |  | 1/8 | 5 | 1 | 0 | 2 | 9 | 3 | 0 | 0 | 0 | 0 | 0 | 0 |
|  |  | 1/16 | 0 | 0 | 0 | 0 | 8 | 1 | 0 | 0 | 0 | 0 | 0 | 0 |
| 180 | (structure with NH—CH(C₂H₅)—CH₂—OCH₃, dinitro, dimethyl) (±) | 2 | 8 | 8 | 0 | 9 | 9 | 9 | 0 | 0 | 0 | 0 | 8 | 7 |
|  |  | 1 | 8 | 7 | 0 | 7 | 9 | 9 | 0 | 0 | 0 | 0 | 0 | 0 |
|  |  | 1/2 | 8 | 6 | 0 | 5 | 9 | 8 | 0 | 0 | 0 | 0 | 0 | 0 |
|  |  | 1/4 | 7 | 0 | 0 | 0 | 9 | 5 | 0 | 0 | 0 | 0 | 0 | 0 |
|  |  | 1/8 | 2 | 0 | 0 | 0 | 6 | 2 | 0 | 0 | 0 | 0 | 0 | 0 |
|  |  | 1/16 | 0 | 0 | 0 | 0 | 1 | 3 | 0 | 0 | 0 | 0 | 0 | 0 |

TABLE XII-continued
Herbicidal Activity of Optically Active and Racemic Dinitroaniline Compounds
| Ex. No. | Compound | Rate lb./Acre | LA | PI | MG | BA | CR | PO | WO | CN | CO | SY | SB | VL |
|---|---|---|---|---|---|---|---|---|---|---|---|---|---|---|
| 181 | 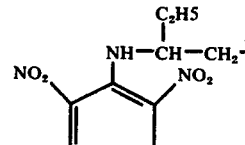 | 4 | 8 | 8 | 6 | 9 | 9 | 9 | 0 | 0 | 0 | 0 | 7 | 6 |
|  |  | 2 | 8 | 7 | 0 | 9 | 9 | 8 | 0 | 0 | 0 | 0 | 6 | 5 |
|  |  | 1 | 8 | 8 | 0 | 7 | 8 | 7 | 0 | 0 | 0 | 0 | 2 | 0 |
|  |  | 1/2 | 7 | 5 | 0 | 5 | 7 | 5 | 0 | 0 | 0 | 0 | 0 | 0 |
|  |  | 1/4 | 2 | 0 | 0 | 0 | 1 | 0 | 0 | 0 | 0 | 0 | 0 | 0 |
|  |  | 1/8 | 0 | 0 | 0 | 0 | 0 | 0 | 0 | 0 | 0 | 0 | 0 | 0 |
|  |  | 1/16 | 0 | 0 | 0 | 0 | 0 | 0 | 0 | 0 | 0 | 0 | 0 | 0 |
| 182 | 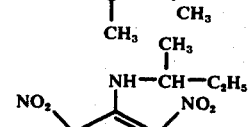 (+) | 1 | 8 | 8 | 0 | 8 | 9 | 9 | 0 | 0 | 2 | 3 | 3 | 7 |
|  |  | 1/2 | 8 | 7 | 0 | 8 | 8 | 9 | 0 | 0 | 0 | 0 | 3 | 6 |
|  |  | 1/4 | 7 | 6 | 0 | 2 | 8 | 8 | 0 | 0 | 0 | 0 | 0 | 0 |
|  |  | 1/8 | 5 | 5 | 0 | 6 | 6 | 8 | 0 | 0 | 0 | 0 | 0 | 0 |
|  |  | 1/16 | 3 | 1 | 0 | 2 | 0 | 7 | 0 | 0 | 0 | 0 | 0 | 0 |
| 183 | 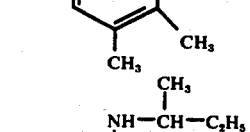 (−) | 1 | 8 | 7 | 0 | 8 | 9 | 9 | 0 | 0 | 3 | 2 | 0 | 0 |
|  |  | 1/2 | 8 | 7 | 0 | 9 | 9 | 9 | 0 | 0 | 0 | 0 | 0 | 0 |
|  |  | 1/4 | 7 | 6 | 0 | 2 | 8 | 8 | 0 | 0 | 0 | 0 | 0 | 0 |
|  |  | 1/8 | 0 | 0 | 0 | 0 | 6 | 8 | 3 | 0 | 0 | 0 | 0 | 0 |
|  |  | 1/16 | 0 | 0 | 0 | 0 | 3 | 7 | 0 | 0 | 0 | 0 | 0 | 0 |
| 184 | 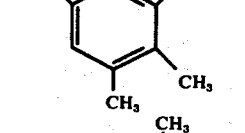 (±) | 1 | 3 | 5 | 0 | 8 | 8 | 8 | 0 | 3 | 2 | 0 | 0 | 0 |
|  |  | 1/2 | 3 | 0 | 0 | 7 | 2 | 8 | 0 | 0 | 0 | 8 | 0 | 0 |
|  |  | 1/4 | 1 | 0 | 0 | 7 | 0 | 7 | 0 | 0 | 0 | 0 | 0 | 0 |
|  |  | 1/8 | 0 | 0 | 0 | 3 | 0 | 1 | 0 | 0 | 0 | 0 | 0 | 0 |
|  |  | 1/16 | 0 | 0 | 0 | 0 | 0 | 0 | 0 | 0 | 0 | 0 | 0 | 0 |
| 185 | 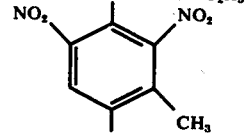 (+) | 2 | 8 | 8 | 5 | 8 | 9 | 8 | 6 | 7 | 0 | 0 | 6 | 7 |
|  |  | 1 | 8 | 8 | 0 | 8 | 9 | 8 | 3 | 3 | 0 | 0 | 5 | 5 |
|  |  | 1/2 | 7 | 7 | 0 | 8 | 8 | 8 | 0 | 0 | 0 | 0 | 3 | 3 |
|  |  | 1/4 | 6 | 6 | 0 | 7 | 8 | 7 | 0 | 0 | 0 | 0 | 2 | 2 |
|  |  | 1/8 | 6 | 5 | 0 | 5 | 8 | 7 | 0 | 0 | 0 | 0 | 0 | 0 |
| 186 | 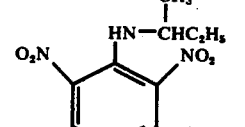 (−) | 2 | 8 | 8 | 2 | 8 | 9 | 8 | 6 | 6 | 0 | 0 | 6 | 6 |
|  |  | 1 | 8 | 8 | 0 | 8 | 9 | 8 | 0 | 6 | 0 | 0 | 3 | 5 |
|  |  | 1/2 | 7 | 7 | 0 | 8 | 8 | 8 | 0 | 0 | 0 | 0 | 0 | 0 |
|  |  | 1/4 | 5 | 5 | 0 | 5 | 8 | 8 | 0 | 0 | 0 | 0 | 0 | 0 |
|  |  | 1/8 | 0 | 0 | 0 | 0 | 6 | 6 | 0 | 0 | 0 | 0 | 0 | 0 |
| 187 | 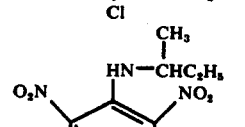 (±) | 2 | 8 | 9 | 2 | 9 | 9 | 8 | 2 | 3 | 0 | 0 | 7 | 6 |
|  |  | 1 | 8 | 8 | 3 | 8 | 9 | 8 | 3 | 2 | 0 | 0 | 3 | 5 |
|  |  | 1/2 | 8 | 8 | 0 | 8 | 9 | 8 | 0 | 0 | 0 | 0 | 0 | 0 |
|  |  | 1/4 | 7 | 7 | 0 | 8 | 9 | 8 | 0 | 0 | 0 | 0 | 0 | 0 |
|  |  | 1/8 | 5 | 5 | 0 | 7 | 8 | 7 | 0 | 0 | 0 | 0 | 0 | 0 |
| 188 | 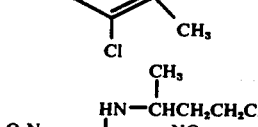 (−) | 2 | 8 | 8 | 0 | 8 | 9 | 7 | 7 | 4 | 0 | 0 | 7 | 6 |
|  |  | 1 | 8 | 8 | 0 | 8 | 9 | 9 | 5 | 0 | 0 | 0 | 3 | 5 |
|  |  | 1/2 | 7 | 7 | 0 | 8 | 8 | 8 | 3 | 0 | 0 | 0 | 0 | 0 |
|  |  | 1/4 | 7 | 5 | 0 | 7 | 8 | 8 | 0 | 0 | 0 | 0 | 0 | 0 |
|  |  | 1/8 | 3 | 3 | 0 | 3 | 8 | 5 | 0 | 0 | 0 | 0 | 0 | 0 |

We claim:

1. A compound of the formula:

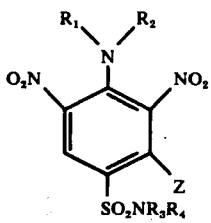

wherein

Z is methyl;

$R_1$ is hydrogen, alkyl $C_1$–$C_6$, alkenyl $C_2$–$C_6$ or alkynyl $C_2$–$C_6$;

$R_2$ is alkyl $C_2$–$C_7$ and may be straight, branched or cyclo; and $R_3$ and $R_4$ each is hydrogen or alkyl $C_1$–$C_4$.

2. The compound of claim 1 of the formula:

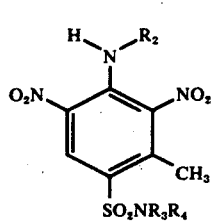

wherein $R_2$ is secondary alkyl $C_2$–$C_6$ and $R_3$ and $R_4$ are hydrogen or methyl.

3. The compound of claim 2: N-sec-butyl-3-methyl-4-(methylsulfamoyl)-2,6-dinitroaniline.

4. The compound of claim 2: N-sec-butyl-3-methyl-4-(dimethylsulfamoyl-2,6-dinitroaniline.

5. The compound of claim 2: N-sec-butyl-3-methyl-4-sulfamoyl-2,6-dinitroaniline.

6. The compound of claim 1: 3-methyl-2,6-dinitro-N,N-di-n-propyl-4-sulfamoylaniline.

7. The compound of claim 2: 4-(dimethylsulfamoyl)-3-methyl-2,6-dinitro-N-3-pentylaniline 8. The compound of claim 1: N,N-di-n-propyl-3-methyl-4-(methylsulfamoyl)-2,6-dinitroaniline.

9. The compound of claim 1: N,N-di-n-propyl-3-methyl-4-(dimethylsulfamoyl)-2,6-dinitroaniline.

10. The compound of claim 1: N,N-di-n-propyl-3-methyl-4-(sec-butylsulfamoyl)-2,6-dinitroaniline.

* * * * *